(12) United States Patent
DeGraaf et al.

(10) Patent No.: US 10,321,923 B2
(45) Date of Patent: Jun. 18, 2019

(54) DEVICES FOR MEDICAL RETRIEVAL PROCEDURES AND METHODS OF USE THEREOF

(71) Applicant: Boston Scientific Scimed, Inc., Maple Grove, MN (US)

(72) Inventors: Kimberly DeGraaf, Holden, MA (US); Mayur Kiran Patel, Framington, MA (US); Jonathan Zoll, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 224 days.

(21) Appl. No.: 14/989,283

(22) Filed: Jan. 6, 2016

(65) Prior Publication Data

US 2016/0213387 A1 Jul. 28, 2016

Related U.S. Application Data

(60) Provisional application No. 62/106,543, filed on Jan. 22, 2015.

(51) Int. Cl.
*A61B 17/221* (2006.01)
*A61B 1/018* (2006.01)
*A61B 17/22* (2006.01)
*A61B 17/00* (2006.01)

(52) U.S. Cl.
CPC ............ *A61B 17/221* (2013.01); *A61B 1/018* (2013.01); *A61B 2017/003* (2013.01); *A61B 2017/0034* (2013.01); *A61B 2017/22078* (2013.01); *A61B 2217/005* (2013.01); *A61B 2217/007* (2013.01)

(58) Field of Classification Search
CPC .. A61B 17/221; A61B 2017/2212–2017/2217; A61B 1/005–1/0058; A61B 17/32056
USPC ........ 600/104, 135, 137, 146; 606/113, 114, 606/127, 128
See application file for complete search history.

(56) References Cited

U.S. PATENT DOCUMENTS

| | | | | |
|---|---|---|---|---|
| 4,748,969 | A * | 6/1988 | Wardle | A61B 1/0051 138/120 |
| 4,750,477 | A * | 6/1988 | Wardle | A61B 1/0051 600/133 |
| 5,169,568 | A * | 12/1992 | Ainger, III | A61B 1/015 264/1.25 |
| 6,162,209 | A * | 12/2000 | Gobron | A61B 17/2909 606/1 |
| 6,743,237 | B2 | 6/2004 | Dhindsa | |
| 8,517,984 | B2 * | 8/2013 | Barenboym | A61M 25/0136 600/131 |

(Continued)

*Primary Examiner* — Kathleen S Holwerda
(74) *Attorney, Agent, or Firm* — Bookoff McAndrews, PLLC

(57) ABSTRACT

Medical devices performing diagnostic and/or treatment procedures, such as retrieving autogenous materials and/or foreign materials from a patient are disclosed. The medical device may comprise a handle, a shaft coupled to the handle, and a retrieval device movably disposed within a working channel of the shaft. The handle may include a steering mechanism for deflecting a deflect a distal end of the shaft and a control mechanism for translating the retrieval device within the working channel. The retrieval device may be integrated into the medical device.

15 Claims, 7 Drawing Sheets

(56) References Cited

U.S. PATENT DOCUMENTS

| | | | |
|---|---|---|---|
| 2003/0109889 A1* | 6/2003 | Mercereau | A61B 17/221 606/127 |
| 2005/0250983 A1* | 11/2005 | Tremaglio | A61B 1/0052 600/101 |
| 2006/0258955 A1* | 11/2006 | Hoffman | A61B 10/06 600/564 |
| 2008/0039684 A1 | 2/2008 | Clayman et al. | |
| 2013/0190561 A1 | 7/2013 | Oskin et al. | |
| 2014/0316203 A1* | 10/2014 | Carroux | A61B 1/00133 600/146 |

* cited by examiner

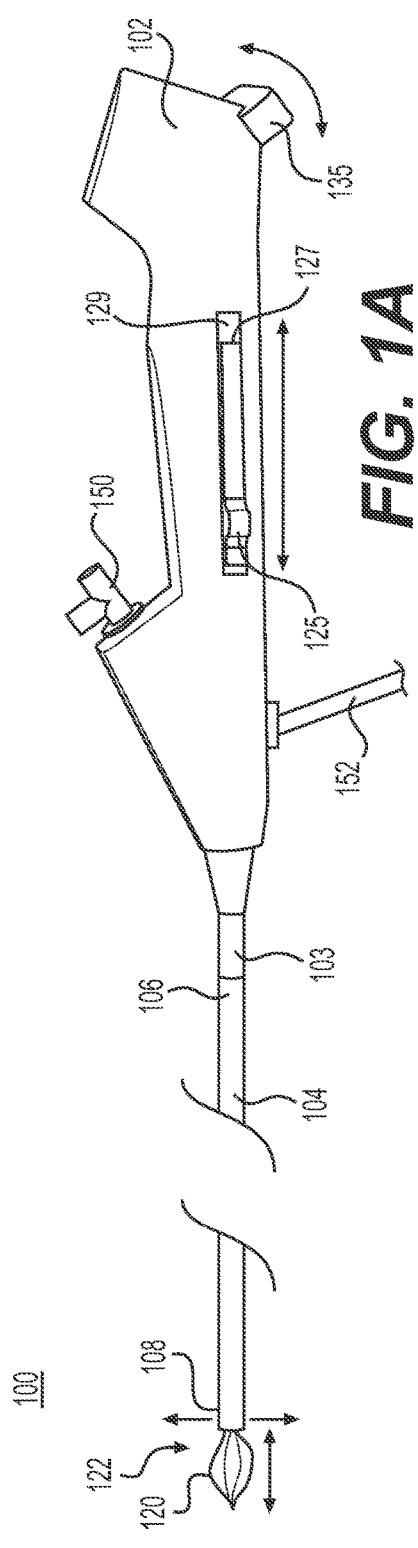
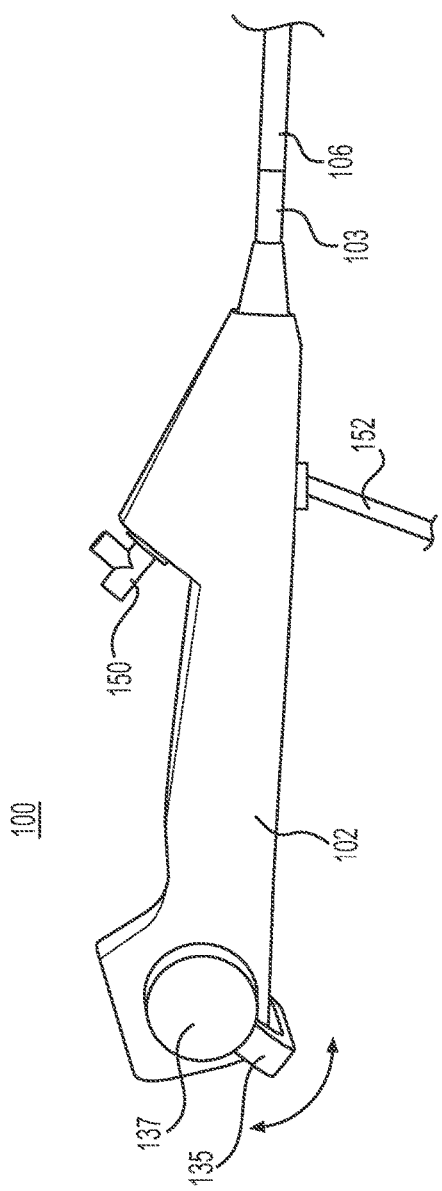
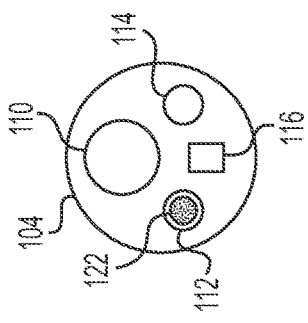

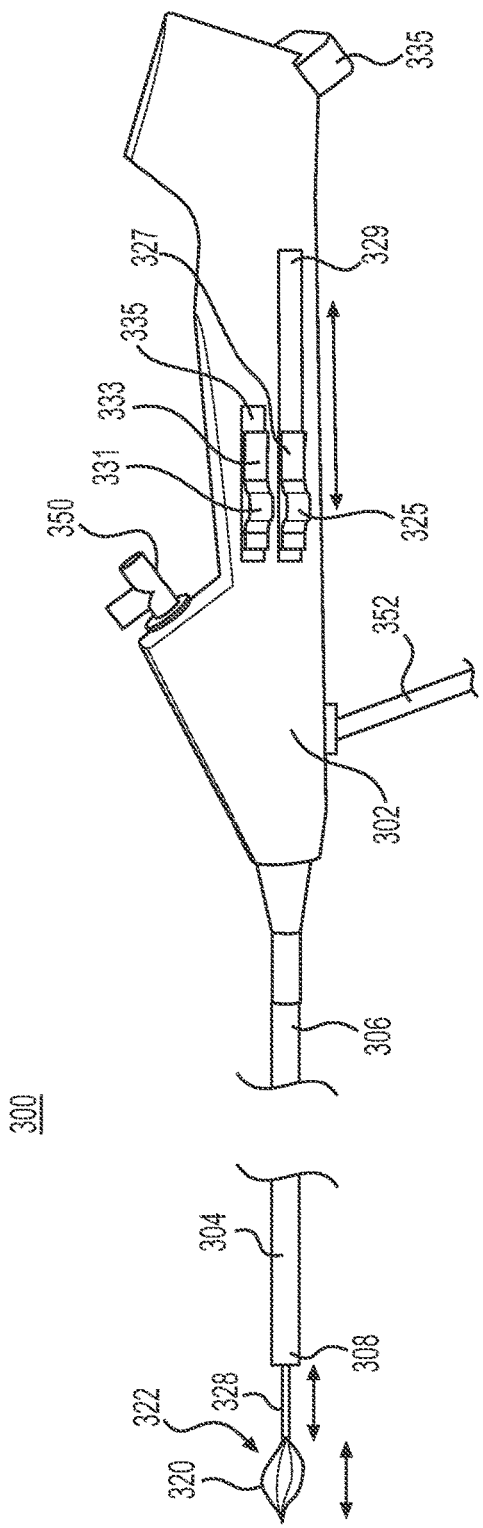
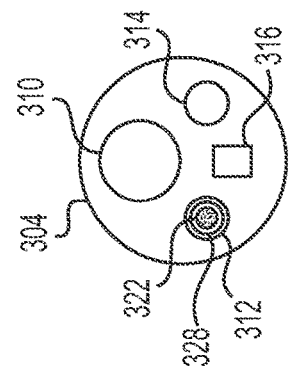
FIG. 3A
FIG. 3B

DEVICES FOR MEDICAL RETRIEVAL PROCEDURES AND METHODS OF USE THEREOF

CROSS-REFERENCE TO RELATED APPLICATIONS

This patent application claims the benefit of priority under 35 U.S.C. § 119 to U.S. Provisional Patent Application No. 62/106,543, filed Jan. 22, 2015, which is herein incorporated by reference in its entirety.

TECHNICAL FIELD

Various aspects of the present disclosure relate generally to medical devices useful in retrieving and removing tissue or other materials from within a patient. More specifically, the present disclosure includes medical devices with integrated tool manipulation and/or relative rotation capability, and methods of use thereof.

BACKGROUND

Retrieval devices and systems allow physicians and other medical professionals to remove various materials from a patient, including organic material (e.g., blood clots, tissue, and biological concretions such as urinary, biliary, and pancreatic stones) and inorganic material (e.g., components of a medical device or other foreign matter). For example, concretions can develop in the kidneys, pancreas, ureter, or gallbladder, and cause blockages or other complications within the body. Minimally-invasive medical procedures may be used to remove these materials through a natural orifice, such as lithotripsy and ureteroscopy, or through an incision, such as percutaneous nephrolithotomy.

Current endoscopic systems have disadvantages, however. For example, ureteroscopic procedures typically require two or more people, wherein a physician controls the ureteroscope with both hands (one hand to grasp the handle and the other to hold the distal portion of the ureteroscope as it enters the urinary tract via the urethral meatus), and an assistant inserts a tool such as a basket, forceps, or a laser through a working channel of the ureteroscope and manipulates the tool. To remove a kidney stone, for example, a ureteroscope is used to gain access to the kidney, and a separate basket device is inserted into the working channel of the ureteroscope to remove or reposition the stone. In order to fragment larger stones into smaller pieces for removal, the basket device can be withdrawn from the working channel and substituted for a laser. After fragmenting the stone, the laser can be removed from the working channel and the basket device reinserted to capture the fragments.

This technique requires careful coordination. If communication between the physician and assistant is unclear, the assistant may require multiple attempts to successfully fragment and retrieve a stone or other material from the patient. Multiple attempts can increase risk to the patient, increase procedure time, and lead to tool damage for repeated unsuccessful attempts. Further, coordination between multiple people to control separate instruments simultaneously in a limited space can be logistically difficult and inconvenient, requiring awkward gripping and imprecise manipulation of the instruments.

SUMMARY

The present disclosure includes a medical device comprising a handle; a shaft coupled to the handle, the shaft including a plurality of working channels; and a retrieval device movably disposed within one of the working channels, wherein the handle includes a steering mechanism configured to deflect a distal end of the shaft and a control mechanism configured to translate the retrieval device within the at least one working channel.

According to some aspects, the retrieval device may include an expandable basket. The control mechanism may include a sliding actuator coupled to the handle for controlling translation of the retrieval device. Additionally or alternatively, the control mechanism may include a locking device for locking a position of the retrieval device.

The handle may include an outer body coupled to an inner body, wherein the inner body is rotatable relative to the outer body, the inner body being coupled to the shaft. In some aspects, for example, the inner body may be rotatable through an arc of up to about 180 degrees, up to about 120 degrees, up to about 90 degrees, up to about 45 degrees, or up to about 30 degrees. Additionally or alternatively, the handle may include at least one port connector in communication with at least one working channel of the plurality of working channels. For example, the handle may include at least one port connector coupled to the outer body and in communication with at least one working channel of the plurality of working channels, wherein rotating the inner body relative to the outer body does not rotate the at least one port connector. The at least one port connector may include a port connector in communication with the at least one working channel, for example. According to some aspects, the medical device may further include a connector configured for at least one of light or data transmission.

According to some aspects of the present disclosure, the steering mechanism of the handle may be configured to deflect a distal end of the shaft along a plurality of planes. For example, the handle may include a first actuator for controlling deflection of the distal end of the shaft along a first plane and a second actuator for controlling deflection of the distal end of the shaft along a second plane transverse to the first plane.

The medical device may further comprise a sheath surrounding at least a portion of the retrieval device, the sheath being disposed within the working channel that includes the retrieval device. The control mechanism of the handle may be configured to translate the retrieval device independently of the sheath. Additionally or alternatively, the control mechanism may be configured to translate the retrieval device and the sheath simultaneously. According to some aspects of the present disclosure, the shaft of the medical device may include at least three working channels. Further, for example, the medical device may be a ureteroscope, wherein the retrieval device is integrated into the ureteroscope.

According to some aspects, the shaft of the medical device may include a first working channel and a second working channel, wherein the first working channel includes the retrieval device and the second working channel is in communication with one or more port connector of the handle. The handle may include an outer body coupled to an inner body, wherein the inner body is rotatable relative to the outer body and coupled to the shaft. The handle may include at least one port connector coupled to the outer body, for example, wherein the port may be in communication with the at least one working channel, and wherein rotating the inner body relative to the outer body does not rotate the at least one port connector.

The present disclosure further includes a medical device comprising a handle including an inner body and an outer body, wherein the outer body at least partially surrounds the inner body; a shaft coupled to the inner body, the shaft including at least one working channel; and a port connector coupled to the outer body, the port connector being in communication with the at least one working channel, wherein the inner body and the shaft are rotatable relative to the outer body and relative to the port connector.

According to some aspects, the medical device may further comprise a retrieval device disposed within the at least one working channel, wherein the inner body includes a control mechanism for translating the retrieval device within the at least one working channel. The shaft of the medical device may include a first working channel and a second working channel, wherein the first working channel includes the retrieval device and at least one of the first working channel or the second working channel is in communication with the port connector. According to some aspects, for example, the medical device may be a ureteroscope, and the retrieval device may include an expandable basket.

The present disclosure further includes a medical device comprising a handle; a shaft coupled to the handle, the shaft including at least two working channels; a retrieval device movably disposed within the at least one working channel, the retrieval device including an expandable basket; and a sheath surrounding at least a portion of the retrieval device and disposed within the at least one working channel, wherein the handle includes a steering mechanism configured to deflect a distal end of the shaft and a control mechanism configured to translate each of the retrieval device and the sheath within the at least one working channel, and wherein the medical device is a ureteroscope. According to some aspects, the retrieval device may be integrated into the medical device, such that the retrieval device is not removable from the shaft.

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

FIGS. 1A-1C show an exemplary medical device, in accordance with aspects of the present disclosure.

FIGS. 3A and 3B show an exemplary medical device, in accordance with aspects of the present disclosure.

DETAILED DESCRIPTION

Figure 2:
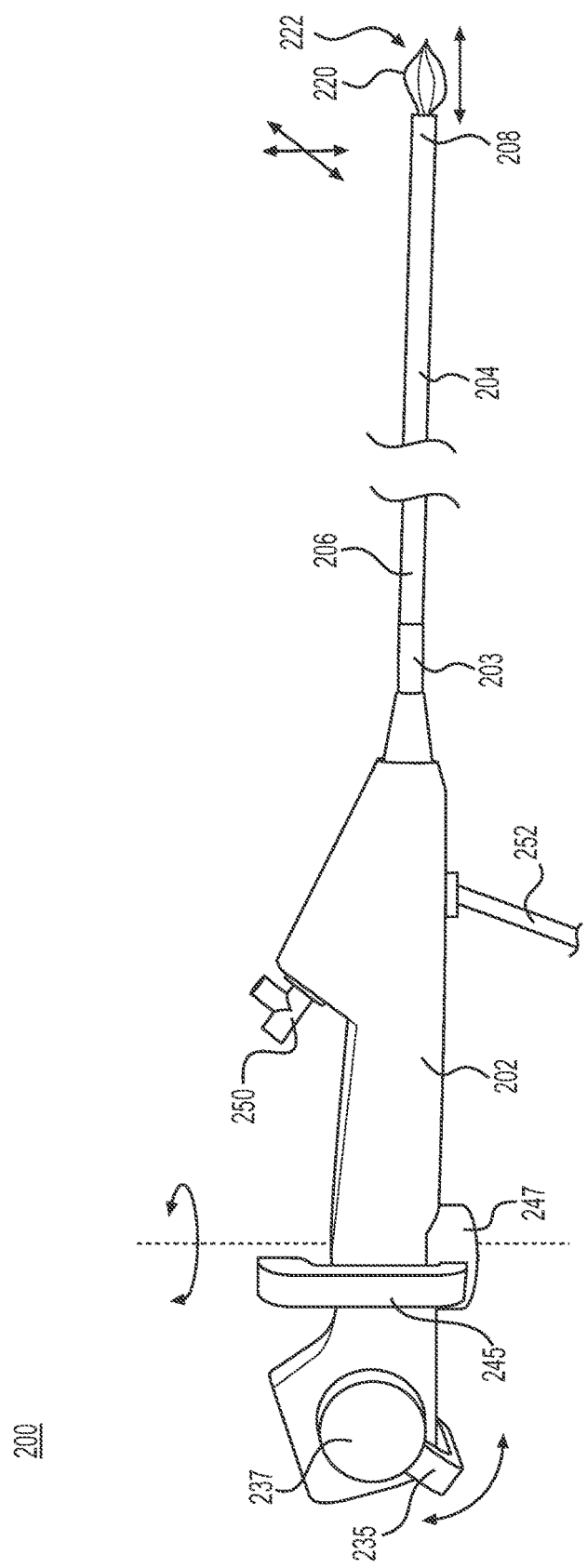
FIG. 2 shows an exemplary medical device, in accordance with aspects of the present disclosure.

Embodiments of the present disclosure include medical devices useful in diagnostic and/or treatment procedures, such as retrieving autogenous materials and/or foreign materials from a patient. Medical devices according to the present disclosure may provide for integrated tool manipulation, for example, and/or rotational control without disturbing attachments coupled to the device via an adapter, such as irrigation or suction channels.

An exemplary medical device 100 according to some aspects of the present disclosure is shown in FIGS. 1A-1C, comprising a handle 102 coupled to a shaft 104. The medical device 100 may be suitable for use in ureteroscopy, for example, but may be configured for use in other procedures and for diagnosis/treatment of other areas of a patient's body. The handle 102 may have any shape suitable for gripping and controlling the medical device 100. For example, the handle 102 may have an ergonomic shape designed to be held comfortably in the hand, e.g., the palm of the hand. The shaft 104 extends from a proximal end 106 to a distal end 108, such that the proximal end 106 of the shaft may be coupled to (e.g., detachably or permanently connected to) the distal end 103 of the handle 102. The handle 102 and/or the shaft 104 may be disposable.

The medical device 100 may include a steering mechanism for deflecting the shaft 104 along one or more planes. For example, the handle 102 may include an actuator 135 coupled to one or more portions of the shaft 104 at or near the distal end 108 of the shaft 104 via one or more control members, such as steering wires (not shown). Any suitable steering mechanism and/or actuators may be used, including those disclosed in U.S. Patent Application Publication No. 2013/0190561, incorporated by reference herein. The actuator 135 may be pivotably coupled to the handle 102 via a post 137, as shown in FIG. 1B, such that pivoting the actuator 135 about the post 137 moves the distal end 108 of the shaft 104 along a plane (e.g., left/right or up/down). According to some aspects, the actuator 135 may include a locking device, such that the actuator 135 may be locked in place when the distal end 108 of the shaft 104 is in a desired position.

The shaft 104 may include at least one working channel, for example three working channels 110, 112, 114 as shown in cross-section in FIG. 1C. According to some aspects, the medical device 100 may include two working channels (e.g., only working channels 110 and 112, or 110 and 114), or may include more than three working channels. Further, the working channels may have different shapes and/or sizes. For example, working channel 110 of FIG. 1C as shown is relatively larger than the other two working channels 112, 114, e.g., such that working channel 110 may serve as a main working channel 110. In some embodiments, the shaft 104 may include one or more electronic components 116, such as a camera or other imaging device, a light source, and/or other sensor. For example, the shaft 104 may include a camera lens ranging from about 0.5 mm$^2$ to about 2 mm$^2$ in size, or from about 0.75 mm$^2$ to about 1.5 mm$^2$ in size, or approximately 1 mm$^2$ in size. Additionally or alternatively, one of the working channels 110, 112, 114, may provide a lumen for light delivery. For embodiments comprising a steering mechanism, the shaft 104 may include control channels (not shown) to house the steering control members.

In some aspects of the present disclosure, the handle 102 may include at least one port 150 in communication with one or more of the working channels 110, 112, 114, e.g., to allow for the insertion of tools (e.g., forceps, scissors, a grasper, a snare, a probe, a guidewire, a laser, an optical device, an imaging device), for irrigation, and/or for suction. For example, an irrigation fluid may be pumped through one or more of the working channels, such as working channel 110 and/or working channel 112, via the port 150 to provide lubrication and/or aid in visualization. The handle 102 may include an electronics hub or connector 152 for electrical connections, such as transferring data and/or powering a light source.

Further referring to FIG. 1C, at least one of the working channels (or according to some aspects of the present disclosure, the only working channel), e.g., channel 112, may house a tool 122 configured to translate proximally and distally, such that the tool 122 may exit the distal end 108 of the shaft 104 for performing a procedure. The tool 122 may be integrated into the medical device 100, such that movement of the tool 122 (e.g., translation) is controlled via a control mechanism of the handle 102. For example, the handle 102 may include a sliding actuator, slide 127, coupled to the tool 122, such that moving the slide 127 with respect to the handle 102 moves the tool 122 with respect to the working channel 112. Moving the slide 127 proximally and distally along the handle 102 may control proximal and distal movement of the tool 122.

The slide 127 may be directly or indirectly coupled to the proximal end of the tool 122 and configured such that moving the slide 127 a certain distance moves the tool 122 the same distance, or a multiple of that distance (e.g., half the distance, two times the distance, three times the distance, etc.). The slide 127 may be configured to slide within a recessed window 129 of the handle 102 as shown in FIG. 1A, Additionally or alternatively, the inner surface of the slide 127 may include an extension that fits into a corresponding groove of the handle, such that the slide 127 moves proximally and distally within the groove to translate the tool 122.

The slide 127 may be located approximately where the user's thumb would be upon gripping the handle 102, such that the thumb may engage the slide 127 to extend and withdraw the tool 122 from the working channel 112. In some embodiments, the slide 127 may include one or more protrusions 125 to facilitate gripping, or to move the slide 127. While only one protrusion 125 is shown in FIG. 1A, according to some aspects of the present disclosure the slide 127 may include a plurality of protrusions 125 (see, e.g., slide 527 of FIG. 5). According to some aspects, the slide 127 may include a locking device, such that the slide 127 may be locked in place, relative to the handle 102, when the tool 122 is in a desired position.

While FIG. 1A illustrates a sliding actuator for controlling translation of the tool 122, other mechanisms may be used. For example, the handle 120 may include a tool actuator configured as a rotatable wheel or a spindle and crank type of mechanism, such that rotating the tool actuator clockwise and counterclockwise with respect to the handle 102 controls proximal and distal translation of the tool 122.

In some aspects of the present disclosure, the tool 122 may comprise an end effector 120, such as a basket as shown in FIG. 1A. For example, the tool 122 may be a basket device configured to capture stones and other materials. Any other suitable tools may be used according to the present disclosure, including, but not limited to, forceps, scissors, a grasper, a snare, a probe, and/or other tools. Tools may comprise materials such as metals, metal alloys, shape memory materials, polymers (including plastics and thermopolymers), or any combinations thereof.

The basket 120 (or other expandable end effector) may be configured to self-expand, wherein basket 120 has a compressed configuration within the working channel 112 and an expanded configuration outside the working channel 112. When in the expanded configuration, outside the distal end 108 of the shaft 104, the basket 120 may be used to retrieve materials and objects captured within the basket 120. For example, the walls of the working channel 112 may serve to compress the basket 120, without the need for a separate sheath or cover. In some aspects this configuration may help to minimize the size of the medical device 100. For example, according to some aspects, the basket device 122 may have a cross-sectional diameter ranging from about 0.5 Fr (0.17 mm) to about 1.5 Fr (0.5 mm), or approximately 1 Fr (0.33 mm); and the working channel 112 may have a cross-sectional diameter ranging from about 1 Fr (0.33 mm) to about 2 Fr (0.67), or approximately 1.5 Fr (0.5 mm).

In some aspects, the basket device 122 may comprise wire, e.g., a wire filament that splits into three, four, or more wires in a generally bulbous shape (basket 120) that converge at the tip. Additionally or alternatively, the basket device 122 may comprise a mesh or net-like portion towards the proximal end of the basket 120, e.g., to capture relatively smaller pieces of materials, such as pulverized stone. Further, for example, the basket 120 may be configured as a net and/or mesh that facilitates the retrieval of small fragments of material. A guidewire and/or laser may be inserted into one of the working channels, such as working channel 110 or 114, during a procedure. For example, a laser may be used to break apart relatively larger pieces of materials within the body to facilitate removal of the material with the basket device 122.

The basket device 122 may comprise Nitinol or other suitable flexible materials. For example, the basket device 122 may comprise Nitinol such that the basket 120 is self-expandable. Alternatively, the basket 120 may be configured to expand manually once extended beyond the distal end 108 of the shaft 104, e.g., via a suitable control mechanism in the handle 102.

Medical devices according to the present disclosure may include a steering mechanism to deflect the shaft along one plane as mentioned above (e.g., via a single actuator, such as actuator 135 of medical device 100 in FIGS. 1A and 1B), or along a plurality of planes, as illustrated by medical device 200 in FIG. 2. Medical device 200 may include any of the features of medical device 100 discussed above. Thus, the medical device 200 may comprise a handle 202 including one or more ports 250 and an electronics connector 252, and a shaft 204 coupled to the distal end 203 of the handle 202, the shaft 204 extending from proximal end 206 to distal end 208. Further, a tool 222 may be disposed within the shaft 204 and include an expandable end effector 220, which may be controlled by a sliding actuator on the handle 202.

The handle 202 may include two actuators for controlling the shaft 204: a first actuator 235 for deflecting the shaft 204 along a first plane (e.g., xy plane), and a second actuator 245 for deflecting the shaft 204 along a second plane (e.g., yz plane). First and second actuators 235, 245 may include any of the features of actuator 135 of medical device 100 discussed above. For example, each actuator 235, 245 may be coupled to the shaft 204 via one or more control members, and may be pivotably coupled to the handle 202 via posts 237, 247, respectively. Thus, rotating the actuators 235, 245 about their respective posts 237, 247 (see arrows in FIG. 2) may move the distal end 208 of the shaft 204 along different planes. The actuators 235, 245 may be controlled independently of each other, or may be used in concert to provide for 360 degree deflection of the shaft 204. In some aspects, the actuators 235, 245 may be oriented such that they rotate about axes that are transverse to each other, e.g., axes that are orthogonal to each other. According to some aspects, one or both of the actuators 235, 245 may include a locking device, such that either or both of actuators 235, 245 may be locked in place when the distal end 208 of the shaft 204 is in a desired position. Any suitable steering mechanism and/or actuators for controlling deflection along a plurality of planes may be used, including those disclosed in U.S. Patent Application Publication No. 2013/0190561, incorporated by reference herein.

In some aspects of the present disclosure, the medical devices may provide for extension of a basket device beyond the distal end of the shaft, e.g., before, during, or after expansion of the basket end effector. FIGS. 3A and 3B illustrate an exemplary medical device 300, which may include any of the features of medical device 100 and/or medical device 200 discussed above. Thus, the medical device 300 may comprise a handle 302 including one or more ports 350 and an electronics connector 352, and a shaft 304 extending from a proximal end 306 to a distal end 308. Further, a basket device 322 may be disposed within a working channel 312 of the shaft 304 and include an expandable basket end effector 320. As shown in cross-section in FIG. 3B, the shaft 304 may include additional working channels, such as working channels 310 and 314, and may include one or more electronic components 316, such as any combination of electronic components 116 discussed in connection to medical device 100 above.

The basket device 322 may include any of the features of tool 122 discussed in connection to medical device 100 above. For example, the basket device 322 may be integrated into the medical device 300, such that movement of the basket device 322 (e.g., translation and/or rotation) is controlled via a control mechanism of the handle 302. In some aspects, at least a portion of the basket device 322 may be covered by a sheath 328. For example, when the basket device 322 is in a retracted position, the entire length of the basket device 322 may be covered by the sheath 328, and when the basket device 322 is in an extended position, only a proximal portion of the basket device 322 may be covered by the sheath 328, the basket end effector 320 being uncovered in the extended position. Exemplary materials suitable for the sheath 328 include stretchable and/or flexible materials, including, but not limited to, polymers.

Each of the sheath 328 and the basket device 322 may be translated relative to the working channel 312 and relative to each other. For example, the handle 302 may include a control mechanism comprising a first slide 327 configured to slide within a recessed window 329 of the handle 302, and a second slide 333 configured to slide within a recessed window 335. The recessed windows 329, 335 for the first and second slides 327, 333 may be different sizes as shown in FIG. 3A, e.g., to allow the slides 327, 333 to slide different lengths along the handle 302. According to some aspects, however, the recessed windows 329, 335 may be approximately the same size. Although shown as being parallel, either of windows 329, 335 and slides 327, 333 may also be oriented transversely to favor certain ergonomic configurations.

Each of the first slide 327 and the second slide 333 may include one or more protrusions, e.g., first protrusion 325 and second protrusion 331, respectively, to facilitate gripping by a user, e.g., with the thumb. The first and second protrusions 325, 331 may be located approximately where the user's thumb would be (or accessible by the thumb) upon gripping the handle 302. The first and second protrusions 325, 331 may have generally the same shape and size, or may have different shapes and/or sizes to allow the user to distinguish between them for controlling the sheath 328 and the basket device 322.

According to some aspects, the first slide 327 may be configured to control (e.g., translate) the basket device 322, and the second slide 333 may be configured to control (e.g., translate) the sheath 328. For example, first slide 327 may be coupled to the proximal end of the basket device 322, and the second slide 333 may be coupled to the proximal end of the sheath 328.

Moving the second slide 333 (e.g., by applying force to the second protrusion 331) proximally and distally with respect to the handle 302 may translate the sheath 328 relative to the basket device 322 and relative to the working channel 312. Thus, for example, the user first may move the second slide 333 to extend the sheath 328 distally beyond the distal end 308 of the shaft 304. While covered by the sheath 328, the basket 320 may be in a retracted and compressed configuration suitable for translation within the working channel 312, and/or within a body passageway prior to expansion.

The user then may move the first slide 327 (e.g., by applying force to the first protrusion 325) proximally and distally to translate the basket device 322 distally through the sheath 328 until the entire basket 320 is uncovered. Once uncovered, the basket 320 may expand into a deployed, expanded configuration as shown in FIG. 3A. The length of the windows 329, 335 for the first and second slides 327, 333 may allow for sufficient freedom of movement of the basket device 322 and the sheath 328 relative to the working channel 312 and relative to each other.

The basket 320 may be self-expandable or manually expandable, as discussed in connection to basket 120 above. Upon capturing material within the basket 320, the basket device 322 may be withdrawn proximally, e.g., by moving the first slide 327 proximally. The shaft 304 then may be withdrawn and removed from the patient. In some aspects, the sheath 328 may be sufficiently flexible to allow the basket 320 and trapped material to be at least partially or completely withdrawn within and surrounded by the sheath 328, wherein the sheath 328 may apply a force radially inward to help to compress the trapped material for removal.

While FIG. 3A illustrates the first and second slides 327, 333 on the same side of the handle 302, e.g., for control by the user's thumb, according to some aspects the first and second slides 327, 333 may be on opposite sides of the handle 302, e.g., for control by the user's thumb and index (or other) finger. For example, the first slide 327 may be located on one side of the handle 302 approximately where of the user's thumb would be (e.g., as shown in FIG. 3A), and the second slide 333 may be located on the opposite side (not visible in FIG. 3A) approximately where the user's index finger would be. Thus, the handle 302 may have a generally ergonomic design to allow the user to control both slides 327, 333 without repositioning his/her hand.

While FIG. 3B illustrates the basket device 322 and the sheath 328 being disposed within working channel 312, e.g., without sufficient room for the passage of an additional tool (e.g., a guidewire, a laser, etc.) through the working channel 312 at the same time. According to some aspects, the basket device 322 and the sheath 328 may be disposed within a relatively larger working channel, such as working channel 310, so that the basket device 322 and the sheath 328 may occupy only a portion of the working channel 310. This configuration allows the remainder of the working channel 310 to be used for insertion of other tools, such as those for irrigation, or for suction.

As an alternative or in addition to the features described above, medical devices according to the present disclosure may provide for rotational control without rotating and disturbing external connections, such as connections for irrigation, suction, tools, or electronic components such as power supply or data transfer.

Figure 4A:
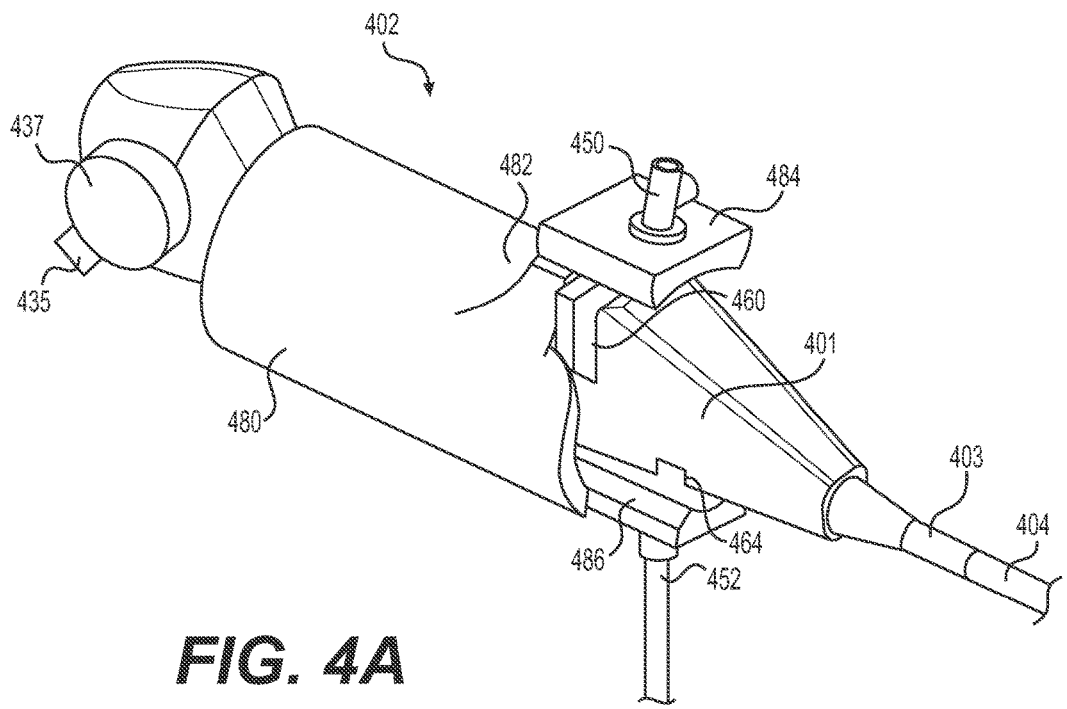
FIGS. 4A-4C show an exemplary medical device, in accordance aspects of the present disclosure.
Figure 4B:
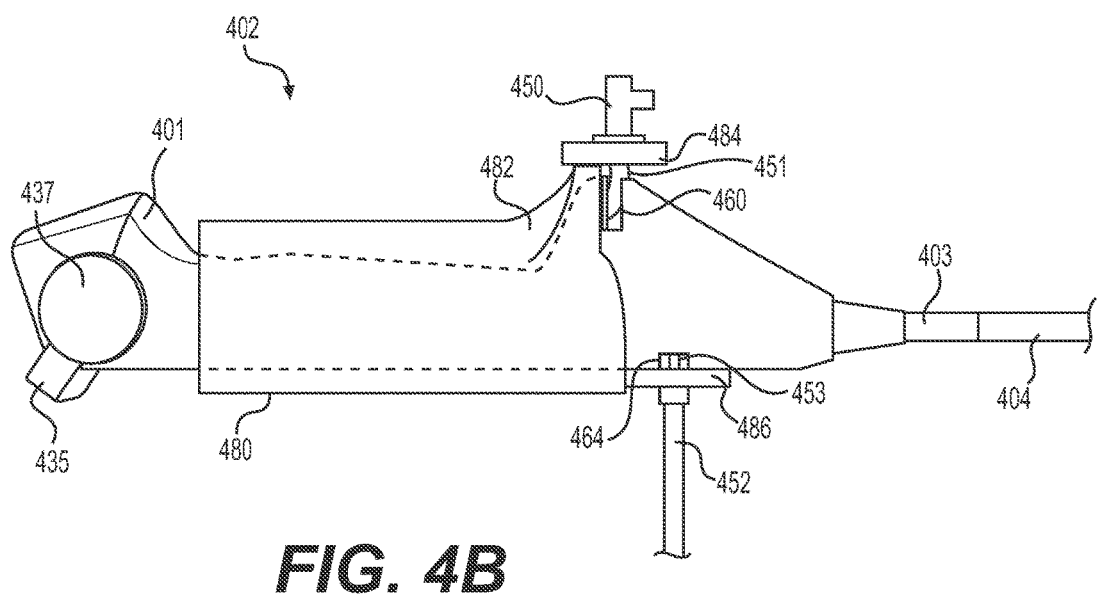
Figure 4C:
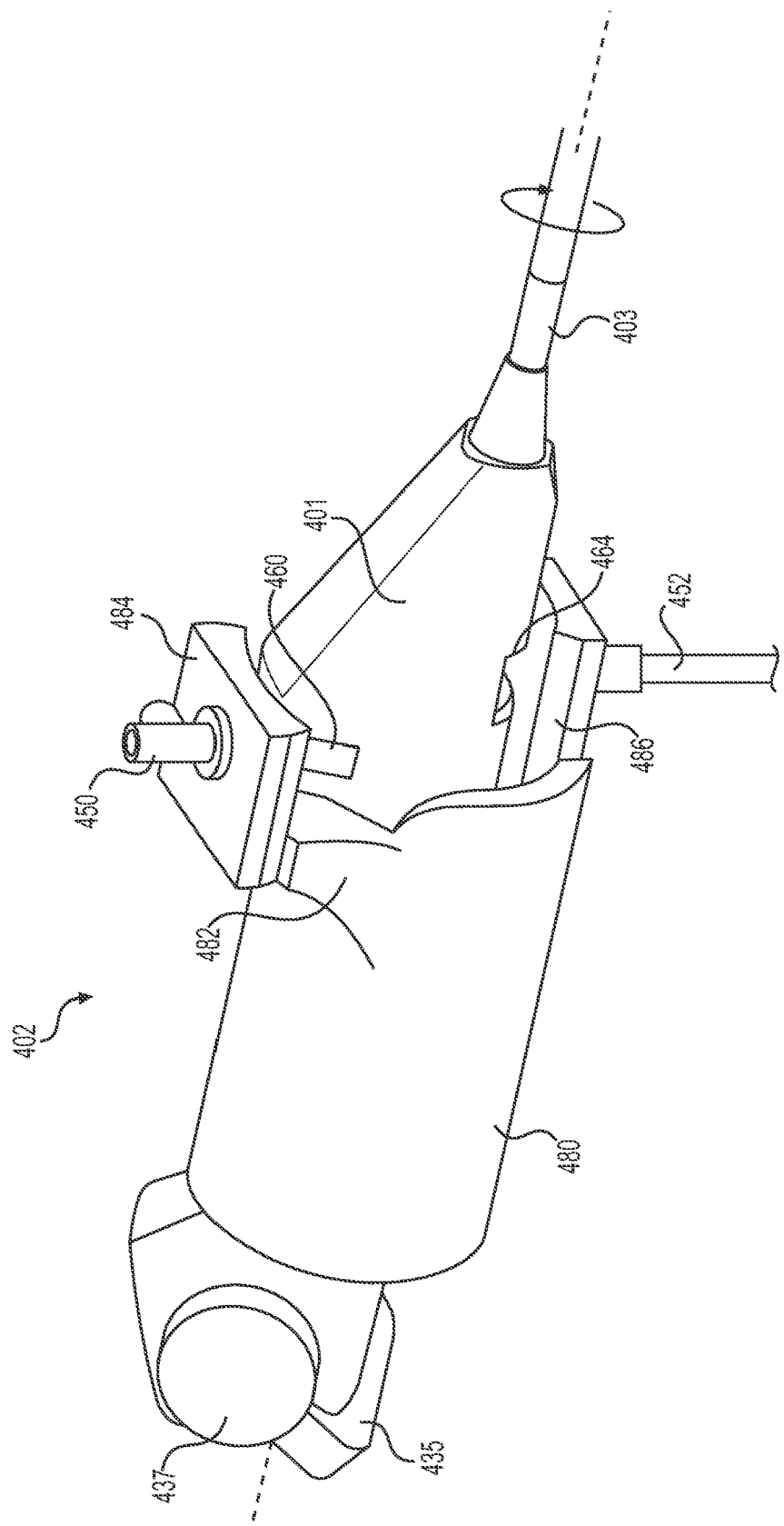

FIGS. 4A-4C illustrate an exemplary handle 402 of a medical device, e.g., configured for detachable or permanent connection to a suitable shaft having one or more working channels. According to some aspects of the present disclosure, for example, the distal end 403 of an inner body 401 of the handle 402 may be configured for attachment to a shaft 404 of similar or otherwise compatible external dimensions, such as any of shafts 104, 204, or 304 discussed above. In particular, shaft 404 may include some or all of the features of shaft 104 shown in FIGS. 1A-1C; these features will be referenced below regarding shaft 404.

The handle 402 may include the inner body 401 and an outer body 480 disposed at least partially around the inner body 401. The inner and outer bodies 401, 480 may be coupled together and rotatable relative to each other, as discussed further below. FIGS. 4A and 4B show perspective and side views, respectively, of the handle in a first position. FIG. 4C shows the handle 402 in a second position where the inner body 401 has been rotated relative to the outer body 440, e.g., about a longitudinal axis of the inner body 401. The handle 402 may have any suitable shape for gripping and controlling the distal portion of the medical device. For example, the inner body 401 and outer body 480 may have a generally ergonomic shape such that the outer body 480 may be held comfortably in the palm of a user's hand.

The handle 402 may include any features of handles 102, 202, or 302 above. According to some aspects of the present disclosure, the handle 402 may include a steering mechanism for controlling the distal end of the medical device (e.g., distal end of shaft 404). For example, the handle 402 may include at least one actuator 435 pivotably coupled to the inner body 401 via a post 437. The actuator 435 and/or post 437 may be coupled to the distal portion of the medical device (e.g., at or near the distal end of the shaft 404) via control members to provide for movement along a plane (e.g., left/right or up/down) as discussed above. In some aspects, the handle 402 may include two or more actuators, e.g., such as first and second actuators 235, 245 of handle 202, to provide for 360 degree deflection (see FIG. 2, discussed above).

The handle 402 may include at least one port 450 (which may include any of the features of ports 150, 250, and/or 350 discussed above) and an electronic connector 452 (which may include any of the features of connectors 152, 252, and/or 352 discussed above). The locations of the port 450 and electronic connector 452 illustrated in FIGS. 4A-4C are exemplary, such that other configurations are possible and encompassed by the present disclosure. For example, the port 450 and the electronics connector 452 both may be disposed on an upper portion of the handle 402, a lower portion of the handle 402, or on one side of the handle 402, or the port 450 and the electronics connector 452 may be disposed on opposite sides of the handle 402.

According to some aspects, the port 450 may provide for access to one or more working channels of the medical device (e.g., working channels 110, 112, 114 of shaft 104), e.g., such that various tools may be inserted into the working channel(s) and exchanged for different tools (e.g., forceps, scissors, a grasper, a snare, a probe, a guidewire, a laser fiber, an optical device, an imaging device), the introduction of fluids (e.g., water or saline for irrigation, contrast dye, etc.) into the working channel(s), and/or for suction via one or more of the working channels. For example, an irrigation fluid may be pumped into the handle 402 via the port 450 to flush out one or more of the working channels, or aid in visualization during a procedure by delivering fluid. For examples in which the handle 402 includes two or more ports 450, each port 450 may be in communication with different working channels of the shaft 404. The electronics connector 452 may be configured for providing light and/or data transmission to a camera or other imaging device. The electronic components may be integrated into the medical device (such as, e.g., electronic component(s) 116 of medical device 100 discussed above).

Both the port 450 and the electronics connector 452 may be coupled to the outer body 480. As shown in FIGS. 4A-4C, for example, the port 450 may be coupled (e.g., fixedly attached) to a mantle 484 of the outer body 480, and the electronics connector 452 may be coupled (e.g., fixedly attached) to a ledge 486 of the outer body 480, opposite the mantle 484. The outer body 480 may include an inclined portion 482 supporting the mantle 484.

The port 450 may lead into the inner body 401 through the mantle 484 and via flexible tubing 451 connecting the mantle 484 to the inner body 401. The tubing 451 may provide a water-tight and/or air-tight connection from the port 450 to the working channel(s) of the medical device. For example, the tubing 451 may extend into an upper slot 460 of the inner body 401 (see, e.g., FIG. 4A) with sufficient slack between the inner and outer bodies 401, 480 to allow the inner body 401 to rotate relative to the outer body 480 without pulling, twisting, crimping, or otherwise compromising the integrity of the water-tight and/or air-tight connection.

Similarly, the electronics connector 452 may lead into the inner body 401 through the ledge 486 and via one or more flexible electronic cables 453, or via flexible tubing housing one or more flexible electronic cables 453. The inner body 401 may include a lower slot 464 (see FIG. 4B) through which the cable 453 may enter into the inner body 401, e.g., with sufficient slack to allow the inner body 401 to rotate relative to the outer body without pulling, twisting, crimping, or otherwise compromising the integrity of the electrical connection. The inner surfaces of the mantle 484 and the ledge 486 may be curved to provide sufficient clearance for the inner body 401 to rotate relative to the outer body 480.

As mentioned above, FIGS. 4A and 4B show the handle 402 in a first, neutral position, before rotation. FIG. 4C shows the handle 402 in a second, rotated position, after the inner body 401 has rotated counterclockwise (from the perspective of the user) about its longitudinal axis and relative to the outer body 480. That is, the outer body 480 and the port 450 and electronic connector 452 attached to the outer body 480 maintain the same position, while the inner body 401 and the shaft 404 coupled to the inner body 401 rotate. Thus, the user may reposition tools at the distal end of the medical device by rotating the inner body 401 about its longitudinal axis without disturbing connections at port 450 or the electronics connector 452. The inner body 401 may be rotatable through an arc of up to about 180 degrees, up to about 120 degrees, up to about 90 degrees, up to about 45 degrees, or up to about 30 degrees. For example, the inner body 401 may be rotatable through an arc ranging from about 0 degrees to about 90 degrees, from about 5 degrees to about 90 degrees, from about 5 degrees to about 45 degrees, or from about 5 degrees to about 30 degrees. The slots 460, 464 may have dimensions suitable for accommodating the desired arc of rotation, e.g., the inner body 401 having relatively longer slots 460, 464 to allow the inner body 401 to rotate relative to the outer body 480 without straining or compromising connections to the port 450 and the electronics connector 452.

In some aspects, the handle 402 may be coupled to a stand (not shown) to support the handle 402 and facilitate manipulation of the handle 402. The stand may extend to the floor, a table, or other substantially flat surface. For example, the stand may comprise a tripod or other suitable design, and may be adjustable for height and/or incline, and may provide for rotational adjustments to position the handle 402 of the medical device with the proposer orientation relative to a patient. Adjustments may be made manually, such as with a hand crank, or via electronic control. According to some aspects, the stand may be configured to clamp onto a support surface near the patient, such as a table, a bed, or other support. Once the stand properly positioned, the outer body 480 of the handle 402 may be secured to the stand via any suitable mechanism (e.g., a tripod head mount or other detachable connection), such that the outer body 480 does not move relative to the stand. With the outer body 480 secured to the stand, the inner body 401 may be free to rotate relative to the outer body 480 and relative to the stand as discussed above.

Figure 5:
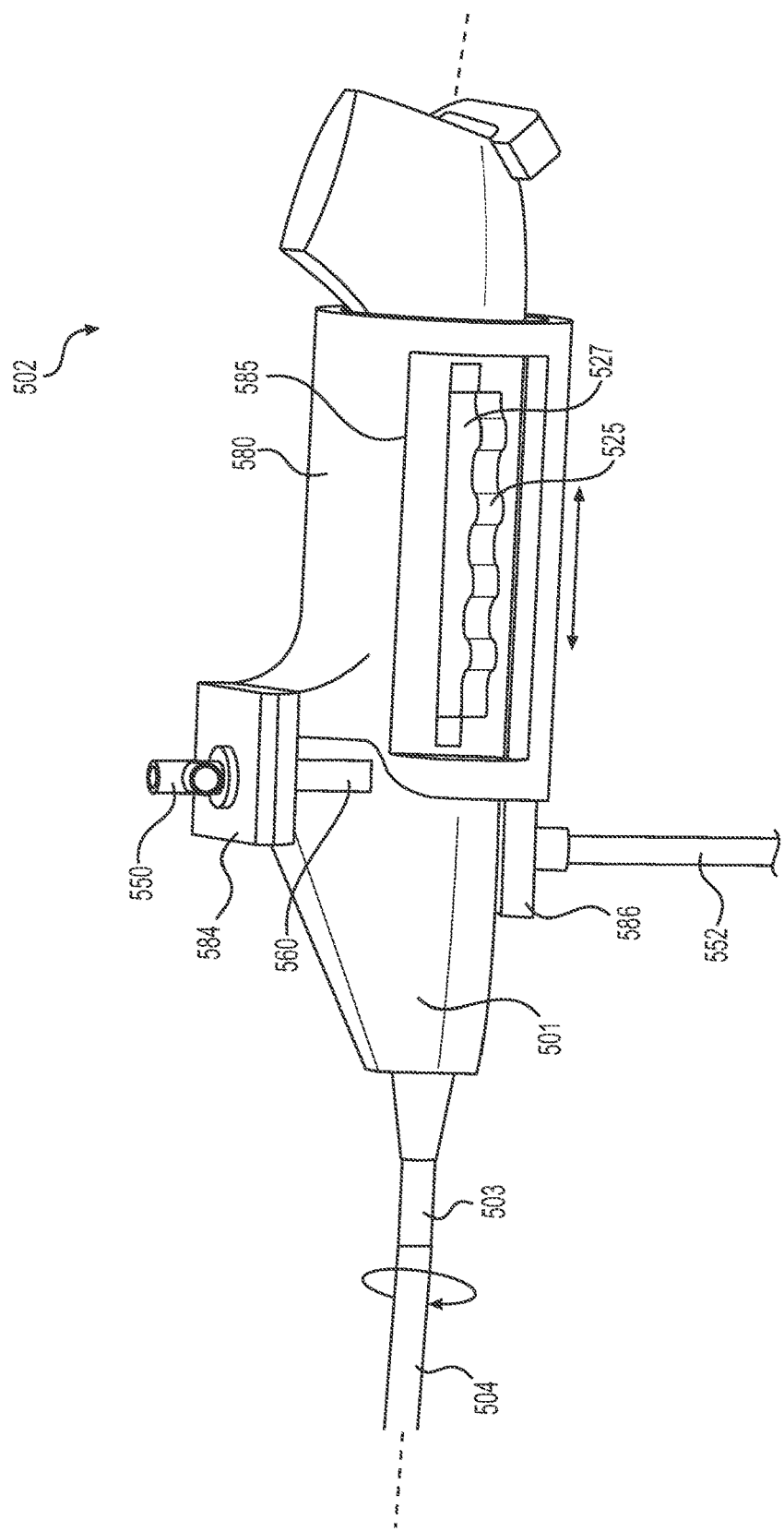
FIG. 5 shows an exemplary medical device, in accordance with aspects of the present disclosure.

Medical devices according to the present disclosure may combine features of the integrated tools discussed in connection to medical device 100 and medical device 300 with the rotational capability discussed in connection to handle 402 above. FIG. 5 illustrates an exemplary handle 502, for example, which may include any of the features of handle 402. Thus, for example, the handle 502 may include an inner body 501 and an outer body 580 at least partially surrounding the inner body 501. The distal end 503 of the inner body 501 may be configured for attachment to a shaft 504 of similar or otherwise compatible external dimensions, such as any of shafts 104, 204, 304, or 404 discussed above. The outer body 580 may be coupled to at least one port 550 (which may include any of the features of ports 150, 250, 350, and/or 450 discussed above) via a mantle 584 and an electronics connector 552 (which may include any of the features of electronics connectors 152, 252, 352, and/or 452 discussed above) via a ledge 586. The inner body 501 may include slots similar to slots 460, 464 of inner body 401 of FIGS. 4A-4C. For example, FIG. 5 shows a slot 560 to accommodate connections via the port 550 (slot corresponding to the electronics connector 552 not shown in FIG. 5).

The handle 502 may include a control mechanism for controlling an integrated tool, such as the mechanisms discussed above for controlling the tool 122 of medical device 100, or the basket device 322 of medical device 300. As shown in FIG. 5, for example, the handle 502 may include a slide 527 coupled to the inner body 501 and movable along the inner body 501, e.g., to control translation of a tool. The slide 527 may include one or more protrusions 525, such as a plurality of protrusions 525 with grooves therebetween to facilitate gripping of the slide 527, accommodate different hand sizes or thumb positions, and/or gripping by multiple fingers. The outer body 580 may include an opening 585 generally aligned with the slide 527 to allow the user to move the slide 527 while gripping the outer body 580. The dimensions of the opening 585 may allow the slide 527 to move freely in proximal and distal directions, and allow for rotation of the inner body 501 relative to the outer body 580 such that the slide 527 may rotate freely clockwise or counterclockwise without contacting the walls of the opening 585. Other control mechanisms may be used as discussed above, such as a rotatable wheel, wherein rotating the wheel corresponds to translation of the tool. Further, while FIG. 5 illustrates a single slide 527, according to some aspects the handle 502 may include two slides, such as first and second slides 327, 333 of handle 302, for controlling a basket device (or other tool) and sheath independently or in combination.

Figure 6:
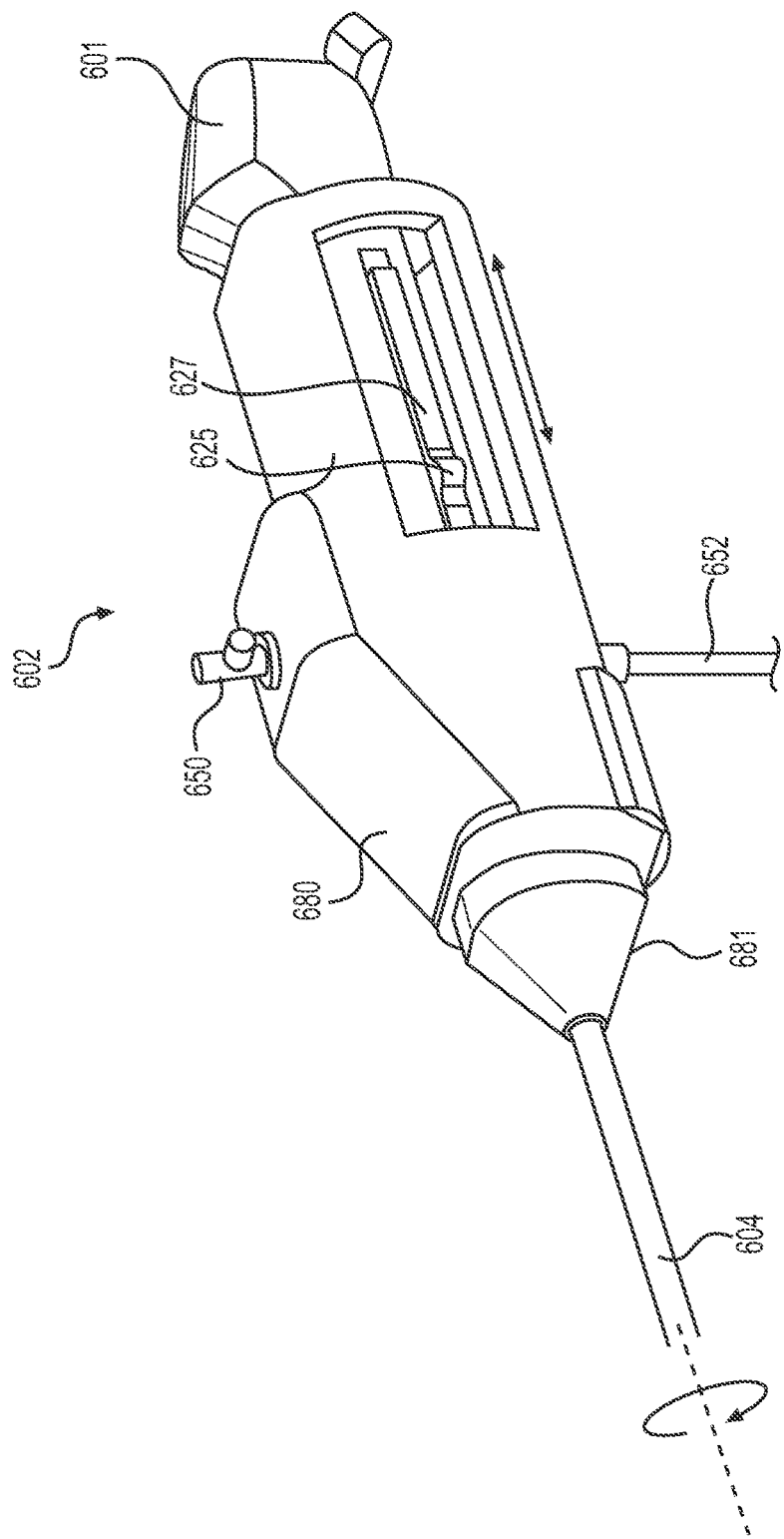
FIG. 6 shows an exemplary medical device, in accordance with aspects of the present disclosure.

FIG. 6 illustrates yet another exemplary handle 602 according to some aspects of the present disclosure. The handle 602 may include any of the features of handles 402 and 502 discussed above. Thus, for example, the handle 602 may include an inner body 601 and an outer body 680 at least partially surrounding the inner body 601. The distal end of the inner body 601 may be coupled to a shaft 604 (which may include any of the features of shafts 104, 204, 304, 404, and/or 504 discussed above), wherein the distal end of the inner body 601 may be entirely covered by the distal end 681 of the outer body 680. As shown in FIG. 6, the shaft 604 may extend through an opening of the distal end 681 of the outer body 680.

The outer body 680 may be coupled to at least one port 650, which may include any of the features of ports 150, 250, 350, 450, and/or 550 discussed above; and an electronics connector 652, which may include any of the features of electronics connectors 152, 252, 352, 452, and/or 552 discussed above. The inner body 601 may include slots (not shown) similar to slots 460, 464 of inner body 401 of FIGS. 4A-4C. Thus, a user may rotate the inner body 601 about its longitudinal axis and relative to the outer body 680, without disturbing connections at the port 650 (e.g., in communication with working channels of the shaft 604) or the electronics connector 652.

The handle 602 may include a control mechanism for controlling an integrated tool, such as the mechanisms discussed above. As shown in FIG. 6, for example, the handle 602 may include a slide 627 (including a protrusion 625) coupled to the inner body 601 and movable along the inner body 601, e.g., to control translation of a tool within a working channel of the shaft 604. The outer body 680 may include an opening generally aligned with the slide 627 to allow the user to move the slide 627 proximally and distally along the inner body 601, and to allow the user to rotate the inner body 601 such that the outer body 680 does not obstruct access to the slide 627.

Further, the inner body 601 and outer body 680 may be coupled together with sufficient clearance, e.g., between the distal end of the inner body 601 and the distal end 681 of the outer body 680, to allow the inner body 601 to rotate freely relative to the outer body 680. Rotating the inner body 601 may rotate the shaft 604 relative to the outer body 680.

Other embodiments of the present disclosure will be apparent to those skilled in the art from consideration of the specification and practice of the embodiments disclosed herein. While certain features of the present disclosure are discussed within the context of exemplary procedures, the devices, instruments, and methods are not so limited and may be used in other areas of the body, and for other medical procedures according to the general principles disclosed. It is intended that the specification and examples be considered as exemplary only, with a true scope and spirit of the present disclosure being indicated by the following claims.

We claim:

1. A medical device comprising:
   a handle including at least one port in a distal portion of the handle, wherein the handle includes a inner body and an outer body at least partially surrounding the inner body and including a port connector, and wherein the inner body extends through the outer body such that a first portion of the inner body extends distally beyond the outer body and a second portion of the inner body extends proximally beyond the outer body;
   a shaft coupled to the handle, the shaft including at least one working channel in communication with the port connector; and a retrieval device movably disposed within the at least one working channel, wherein the handle includes a steering mechanism rotatably or pivotably coupled to a proximal portion of the handle, wherein the steering mechanism is configured to deflect a distal end of the shaft, wherein the handle further includes a control mechanism coupled to the handle distal to the steering mechanism, wherein the control mechanism includes a first actuator coupled to a proximal portion of a retrieval basket wire and configured to translate the retrieval basket wire within the at least one working channel by sliding the first actuator parallel to a longitudinal axis of the handle within a first window, and wherein the control mechanism includes a second actuator coupled to a proximal portion of a sheath, wherein the sheath surrounds at least a portion of the retrieval basket wire, and wherein the second actuator is configured to translate the sheath within the at least one working channel relative to the retrieval basket wire by sliding the second actuator parallel to the longitudinal axis of the handle within a second window in the handle, wherein the first window and the second window are both positioned in a middle portion of the handle distal to the steering mechanism and proximal to the at least one port, and wherein the first window and the second window extend parallel to each other and at least partially overlap over a length of the handle, wherein the inner body and the shaft are rotatable without rotating the outer body, wherein the inner body includes at least one upper slot transverse to the longitudinal axis of the handle, wherein the upper slot houses at least a portion of at least one tube, wherein a distal portion of the outer body includes at least one mantle supporting the port connector, and wherein the at least one tube maintains connection between the port connector and the at least one working channel when the inner body rotates relative to the outer body, and wherein the inner body further includes at least one lower slot transverse to the longitudinal axis of the handle, wherein the lower slot houses at least a portion of at least one electronic cable, wherein the distal portion of the outer body further includes at least one ledge positioned on the distal portion of the outer body opposite to the mantle, wherein the ledge is configured to support at least one electronics connector, and wherein the at least one electronic cable maintains connection between the electronics connector and the inner body when the inner body rotates relative to the outer body.

2. The medical device of claim 1, wherein the retrieval device includes an expandable basket.

3. The medical device of claim 2, wherein the sheath is disposed within the at least one working channel.

4. The medical device of claim 1, wherein the control mechanism includes protrusions coupled to each of the first actuator and the second actuator to aid in controlling translation of the retrieval device and the sheath, and wherein the control mechanism further includes a locking device to lock the first actuator or the second actuator in place relative to the handle.

5. The medical device of claim 1, wherein the electronics connector is configured for at least one of light or data transmission.

6. The medical device of claim 1, wherein the at least one working channel includes a first working channel and a second working channel, wherein the first working channel includes the retrieval device and the second working channel is in communication with the port connector.

7. The medical device of claim 1, wherein the medical device is a ureteroscope, and the retrieval device is integrated into the ureteroscope.

8. The medical device of claim 1, wherein the steering mechanism is configured to deflect the distal end of the shaft along a plurality of planes.

9. A medical device comprising:
a handle including an inner body and an outer body, wherein the outer body at least partially surrounds the inner body, and wherein the inner body extends through the outer body such that a first portion of the inner body extends distally beyond the outer body and a second portion of the inner body extends proximally beyond the outer body;
a shaft coupled to the inner body, the shaft including at least one working channel;
a port connector coupled to the outer body, the port connector being in communication with the at least one working channel;
an electronics connector coupled to the outer body, the electronics connector being in communication with the inner body;
at least one tube connecting the port connector to the at least one working channel; and
at least one electronic cable connecting the electronics connector to a portion of the inner body,
wherein the inner body and the shaft are rotatable relative to the outer body and relative to the port connector such that rotating the inner body relative to the outer body does not rotate the port connector,
wherein the inner body includes at least one upper slot transverse to a longitudinal axis of the handle, wherein the upper slot houses at least a portion of the at least one tube, wherein a distal portion of the outer body includes at least one mantle supporting the port connector, and wherein the at least one tube maintains connection between the port connector and the at least one working channel when the inner body rotates relative to the outer body, and
wherein the inner body further includes at least one lower slot transverse to the longitudinal axis of the handle, wherein the lower slot houses at least a portion of the at least one electronic cable, wherein the distal portion of the outer body further includes at least one ledge positioned on the distal portion of the outer body opposite to the mantle, wherein the ledge is configured to support the electronics connector, and wherein the at least one electronic cable maintains connection between the electronics connector and the inner body when the inner body rotates relative to the outer body.

10. The medical device of claim 9, further comprising a retrieval device disposed within the at least one working channel, wherein the inner body includes a control mechanism for translating the retrieval device within the at least one working channel.

11. The medical device of claim 10, wherein the medical device is a ureteroscope, and the retrieval device includes an expandable basket.

12. The medical device of claim 10, wherein the at least one channel includes a first working channel and a second working channel, wherein the first working channel includes the retrieval device and at least one of the first working channel or the second working channel is in communication with the port connector.

13. A medical device comprising:
a handle having an outer body and an inner body, wherein the inner body includes a distal portion, a proximal portion, and a middle portion between the distal portion and the proximal portion, and wherein the outer body at least partially surrounds the inner body;
a shaft coupled to the handle, the shaft including at least two working channels;
a retrieval device movably disposed within one of the at least two working channels, the retrieval device including an expandable basket; and
a sheath surrounding at least a portion of the retrieval device and disposed within the same working channel as the retrieval device,
wherein the handle includes a steering mechanism configured to deflect a distal end of the shaft and a control mechanism configured to independently translate each of the retrieval device and the sheath within one of the at least two working channels,
wherein the control mechanism includes a first actuator and a second actuator,
wherein the first actuator is translatable parallel to a longitudinal axis of the handle within a first window to control the translation of the retrieval device,
wherein the second actuator is translatable parallel to the longitudinal axis of the handle within a second window to control the translation of the sheath,
wherein the first window and the second window are both positioned in the middle portion of the inner body of the handle, and wherein the first window and the second window extend parallel to each other and at least partially overlap over a longitudinal length of the handle,
wherein the inner body includes at least one upper slot transverse to the longitudinal axis of the handle, wherein the upper slot houses at least a portion of at least one tube connecting at least one port connector on the outer body to one of the at least two working channels,
wherein a distal portion of the outer body includes at least one mantle supporting the at least one port connector,
wherein the at least one tube maintains connection between the at least one port connector and one of the at least two working channels when the inner body rotates relative to the outer body, and
wherein the inner body further includes at least one lower slot transverse to the longitudinal axis of the handle, wherein the lower slot houses at least a portion of at least one electronic cable, wherein a distal portion of the outer body further includes at least one ledge positioned on the distal portion of the outer body opposite to the mantle, wherein the ledge is configured to support at least one electronics connector, and wherein the at least one electronic cable maintains connection between the electronics connector and the inner body when the inner body rotates relative to the outer body.

14. The medical device of claim 13, wherein the medical device is a ureteroscope, and wherein the inner body extends through the outer body such that a first portion of the inner body extends distally beyond the outer body and a second portion of the inner body extends proximally beyond the outer body.

15. The medical device of claim 13, wherein the medical device is a ureteroscope, wherein the retrieval device is integrated into the ureteroscope and not removable from the shaft.

* * * * *